United States Patent
Yamamoto et al.

(10) Patent No.: US 10,519,112 B2
(45) Date of Patent: Dec. 31, 2019

(54) METHOD FOR PRODUCING HETEROAROMATIC SULFONAMIDE COMPOUND

(71) Applicant: UBE INDUSTRIES, LTD., Ube-shi, Yamaguchi (JP)

(72) Inventors: Yasuhito Yamamoto, Ube (JP); Masayoshi Oue, Ube (JP); Masahiko Hagihara, Ube (JP); Yukinori Wada, Ube (JP); Gen Mizuno, Ube (JP); Yasunori Tsuzaki, Ube (JP); Kenichi Arai, Ube (JP)

(73) Assignee: UBE INDUSTRIES, LTD., Ube-Shi (JP)

( * ) Notice: Subject to any disclaimer, the term of this patent is extended or adjusted under 35 U.S.C. 154(b) by 0 days.

(21) Appl. No.: 15/317,875

(22) PCT Filed: Jun. 10, 2015

(86) PCT No.: PCT/JP2015/066688
§ 371 (c)(1),
(2) Date: Dec. 9, 2016

(87) PCT Pub. No.: WO2015/190506
PCT Pub. Date: Dec. 17, 2015

(65) Prior Publication Data
US 2017/0121288 A1    May 4, 2017

(30) Foreign Application Priority Data
Jun. 10, 2014 (JP) ................. 2014-119690

(51) Int. Cl.
*C07D 213/71* (2006.01)
*C07D 401/12* (2006.01)

(52) U.S. Cl.
CPC ......... *C07D 213/71* (2013.01); *C07D 401/12* (2013.01)

(58) Field of Classification Search
CPC ... C07D 213/70; C07D 213/71; C07D 401/12
See application file for complete search history.

(56) References Cited

U.S. PATENT DOCUMENTS

| | | |
|---|---|---|
| 2005/0171180 A1 | 8/2005 | Resnick et al. |
| 2007/0203245 A1 | 8/2007 | Koltun et al. |
| 2008/0214394 A1 | 9/2008 | Puhl et al. |
| 2010/0273739 A1 | 10/2010 | Amberg et al. |
| 2011/0054172 A1 | 3/2011 | Iwamura et al. |
| 2012/0190852 A1 | 7/2012 | Hagihara et al. |
| 2013/0184238 A1 | 7/2013 | Amberg et al. |
| 2014/0031331 A1 | 1/2014 | Amberg et al. |
| 2014/0113907 A1 | 4/2014 | Iwamura et al. |
| 2016/0060221 A1 | 3/2016 | Shibakawa et al. |

FOREIGN PATENT DOCUMENTS

| | | | |
|---|---|---|---|
| CA | 2757291 A1 | 10/2010 | |
| CN | 102911086 A | 2/2013 | |
| JP | 2002-322054 A | 11/2002 | |
| JP | 2011-57633 A | 3/2011 | |
| WO | WO 2007/067817 A1 | 6/2007 | |
| WO | WO 2008/103615 A1 | 8/2008 | |
| WO | WO 2009/083123 A1 | 7/2009 | |
| WO | WO 2009/113600 A1 | 9/2009 | |
| WO | WO 2010/059627 A1 | 5/2010 | |
| WO | WO 2010/113957 A1 | 10/2010 | |
| WO | WO 2010/125831 A1 | 11/2010 | |
| WO | WO 2011011722 * | 1/2011 | ............. A01N 43/56 |
| WO | WO 2011/028741 A1 | 3/2011 | |
| WO | WO 2011/030865 A1 | 3/2011 | |
| WO | WO 2014/157672 A1 | 10/2014 | |
| WO | WO 2016047742 * | 3/2016 | ........... C07D 213/71 |

OTHER PUBLICATIONS

CADDICK. Journal of the American Chemical Society, 2004, 126, 1024-25 (Year: 2004).*
U.S. Appl. No. 15/317,817, filed Dec. 9, 2016.
Effenberger et al., "Darstellung und Reaktionen von Trifluormethansulfonsäure-sulfonsäure-anhydriden," Angewandte Chemie, vol. 86, No. 11, XP002773659, Jan. 1974, pp. 409-410.
Extended European Search Report for European Application No. 15806408.9, dated Oct. 23, 2017.
Brettle et al., "N-Alkylation of Some Secondary Styryl Enamides", J. Chem. Soc. Perkin Trans. I, 1985, pp. 831-836.
Cardullo et al., "Parallel Protocol for the Selective Methylation and Alkylation of Primary Amines," J. Comb. Chem., vol. 8, No. 6, 2006, pp. 834-840.

(Continued)

*Primary Examiner* — Noble E Jarrell
(74) *Attorney, Agent, or Firm* — Birch, Stewart, Kolasch & Birch, LLP

(57) ABSTRACT

The present invention provides: a method for producing a mixed sulfonic acid anhydride of the general formula (1) by reacting a sulfonic acid compound of the general formula (2) with a perfluoroalkyl sulfonic acid anhydride or a perfluoroalkyl sulfonic acid halide; and a method for producing a sulfonamide compound of the general formula (4) obtained by reacting an amine compound of the general formula (3) with a mixed sulfonic acid anhydride of the general formula (1).

1 Claim, No Drawings

(56) References Cited

OTHER PUBLICATIONS

Chernyshev et al., "Alkylation of Acyl and Sulfonyl Derivatives of 3,5-diamino-1-phenyl-1,2,4-triazole," Chemistry of Heterocyclic Compounds, vol. 45, No. 4, 2009, pp. 436-444.

Cirauqui et al., "New Amide Derivatives as Melanin-concentrating Hormone Receptor 1 Antagonists for the Treatment of Obesity", Arzneimittel-Forschung (Drug Research), vol. 58, No. 11, 2008, pp. 585-591.

Hu et al., "2,4-Thiazolidinediones as Potent and Selective Human $\beta_3$ Agonists," Bioorganic & Medicinal Chemistry Letters, vol. 11, 2001, pp. 757-760.

Inoue et al., "Boron-Mediated Aldol Reaction of Carboxylic Esters: Complementary Anti- and Syn-Selective Asymmetric Aldol Reactions," J. Org. Chem., vol. 67, No. 15, 2002 (Published on Web Jun. 26, 2002), pp. 5250-5256.

MacPherson et al., "Discovery of CGS 27023A, a Non-Peptidic, Potent, and Orally Active Stromelysin Inhibitor that Blocks Cartilage Degradation in Rabbits," J. Med. Chem., vol. 40, No. 16, 1997 (Abstract published in Advance ACS Abstracts Jul. 1, 1997), pp. 2525-2532.

Shono et al., "Electrooxidative Rearrangement of Tosylamino Group: Facile Synthesis of α-Amino Aldehydes from Primary Amines," Tetrahedron Letters, vol. 27, No. 50, 1986, pp. 6083-6086.

Written Opinion of the International Searching Authority and English translation of the International Search Report (forms PCT/ISA/237 and PCT/ISA/210), dated Jul. 14, 2015, for International Application No. PCT/JP2015/066689.

Barton et al., "Discovery and optimisation of a potent and selective tertiary sulfonamide oxytocin antagonist," Bioorganic & Medicinal Chemistry Letters, vol. 19, 2009 (available online Nov. 12, 2008), XP025816981, pp. 528-532.

Extended European Search Report issued in European Application No. 15807453.4 dated Jan. 2, 2018.

Fletcher et al., "Structure-Based Design and Synthesis of Potent, Ethylenediamine-Based, Mammalian Farnesyltransferase Inhibitors as Anticancer Agents," Journal of Medicinal Chemistry, vol. 53, No. 19, 2010 (published on Web Sep. 7, 2010), XP055435372, pp. 6867-6888.

Sexton et al., "Inhibitors of Lipoprotein(a) Assembly," Bioorganic & Medicinal Chemistry, vol. 11, 2003, XP001181005, pp. 4827-4845.

Ahmad Shaabani et al., "A novel approach for the synthesis of alkyl and aryl sulfonamides", Tetrahedron Letters, vol. 48, 2007, pp. 2185-2188.

File registry on STN, RN 51567-94-3, Entered STN: Nov. 16, 1984.

International Search Report for PCT/JP2015/066688 (PCT/ISA/210) dated Jul. 14, 2015.

Jason D. Bonk et al., "Convenient One-Pot Synthesis of Sulfonamides from Thiols using Trichloroisocyanuric Acid", Synthetic Communications, vol. 37, 2007, pp. 2039-2050.

Joseph Kelly et al., "Synthesis of Isomeric 3-Piperidinyl and 3-Pyrrolidinyl Benzo[5,6]cyclohepta[1,2-b]pyridines: Sulfonamido Derivatives as Inhibitors of Ras Prenylation", Bioorganic & Medicinal Chemistry, vol. 6, 1998, pp. 673-686.

Stephen W. Wright et al., "A Convenient Preparation of Heteroaryl Sulfonamides and Sulfonyl Fluorides from Heteroaryl Thiols", Journal of Organic Chemistry, vol. 71, 2006, pp. 1080-1084.

Yasuhiro Morisawa et al., "Studies on Anticoccidial Agents. 13. Synthesis and Anticoccidial Activity of Nitropyridine-2- and -3-sulfonamides and Derivatives", Journal of Medicinal Chemistry, vol. 23, 1980, pp. 1376-1380.

Chinese Office Action and Search Report, dated Mar. 6, 2019, for Chinese Application No. 201580031028.4, as well as an English translation of the Chinese Office Action.

Chmielewski et al., "Increasing the Racemase Activity versus Transaminase Activity of a Pyridoxal Enzyme Model by the Attachment of a Rigid Base," Heterocycles, vol. 25, No. 1, Jan. 1987, pp. 533-540.

* cited by examiner

METHOD FOR PRODUCING HETEROAROMATIC SULFONAMIDE COMPOUND

TECHNICAL FIELD

The present invention relates to a mixed sulfonic acid anhydride obtained from a heteroaromatic sulfonic acid compound and a perfluoroalkyl sulfonic acid anhydride or a perfluoroalkyl sulfonic acid halide, and a method for producing a heteroaromatic sulfonamide compound by reacting the mixed sulfonic acid anhydride obtained with amine. The method for producing the heteroaromatic sulfonamide compound of the present invention is safer than conventional methods, and also provides a higher yield and fewer byproducts, so that the method is very useful in industry. Further, the heteroaromatic sulfonamide compound obtained by the production method of the present invention is a useful compound as an intermediate and a drug substance for a medicine.

BACKGROUND ART

Heteroaromatic sulfonamide compounds are useful compounds in various fields as medicinal and agrochemical products and organic materials, or as raw materials and intermediates thereof. In particular, the compounds have recently been reported to be useful as medicinal products, and a safe and convenient production method is still desired (for example, see Non-Patent Document 1).

As a synthesis method of a heteroaromatic sulfonamide compound, a number of methods for producing a sulfonamide compound by reacting heteroaromatic sulfonyl chloride with amine have been reported until now (for example, see Patent Document 1 and Non-Patent Document 2).

In addition, as a synthesis method of a heteroaromatic sulfonamide compound, a method for producing a sulfonamide compound by the reaction of amine with heteroaromatic sulfonyl chloride which has been made using heteroaromatic sulfonic acid and phosphorus pentachloride ($PCl_5$) or phosphorous oxychloride ($POCl_3$) has been reported (for example, see Patent Document 2).

As a synthesis method of a heteroaromatic sulfonamide compound, a method for producing a sulfonamide compound by the reaction of amine with a heteroaromatic sulfonyl chloride which has been made from heteroaromatic thiol as a starting material using sodium hypochlorite or trichloroisocyanuric acid has been reported (for example, see Non-Patent Document 3 and Non-Patent Document 4).

On the other hand, a synthesis method of a heteroaromatic sulfonamide compound by reacting a mixed sulfonic acid anhydride of heteroaromatic sulfonic acid and p-nitrobenzene sulfonic acid with amine has been reported. (for example, see Non-Patent Document 5)

PRIOR ART DOCUMENTS

Patent Documents

Patent Document 1: WO 2010-125831
Patent Document 2: WO 2011-028741

Non-Patent Documents

Non-Patent Document 1: Tetrahedron Letters, 2007, Vol. 48, No. 50, 2185-2188
Non-Patent Document 2: Journal of Medicinal Chemistry, 1980, Vol. 23, No. 12, 1376-1380
Non-Patent Document 3: Journal of Organic Chemistry, 2006, Vol. 71, 1080-1084
Non-Patent Document 4: Synthetic Communication, 2007, Vol. 37, 2039-2050
Non-Patent Document 5: Bioorganic & Medicinal Chemistry, 1998, Vol. 6, 678-686

SUMMARY OF THE INVENTION

Problem to be Solved by the Invention

Heteroaromatic sulfonyl chloride which has been used for synthesis of heteroaromatic sulfonamide compounds until now is water-labile, difficult to be handled, and also undesirable for long-term storage. In addition, this compound is hard to be obtained in a case of the large quantity use, exhibits low heat stability, and is dangerous because of its decomposition by heating and accompanying abnormal heat generation, so that it is undesirable as a compound for the industrial use.

In addition, phosphorus pentachloride ($PCl_5$) and phosphorous oxychloride ($POCl_3$) have a high toxicity and also negative effects on the environment, and furthermore, thiol has a bad odor, so that a method using these compounds is undesirable as an industrial manufacturing method. Further, the use of an oxidizing agent is also undesirable as an industrial production method because the treatment and the like with the agent make the operation complicated.

In addition, in a synthesis method of a heteroaromatic sulfonamide compound by reacting a mixed sulfonic acid anhydride of heteroaromatic sulfonic acid and p-nitrobenzene sulfonic acid with amine, a large amount of p-nitrobenzenesulfonamide compounds are produced as byproducts other than the desired heteroaromatic sulfonamide compound, and complicated work-up such as column chromatography is needed to remove the byproducts.

As described above, as a synthesis method of a heteroaromatic sulfonamide compound, a method which is safe, has a low effect on the environment, produces fewer byproducts, and requires easy work-up, has been desired.

A problem to be solved by the present invention is to provide a production method which is convenient and also industrially preferred, wherein a heteroaromatic sulfonamide compound can be obtained safely and in a good yield.

As a result of conducting extensive studies on methods for synthesizing heteroaromatic sulfonamide compounds, the inventors of the present invention have found out an industrially superior production method for obtaining safe, high-yield and high-purity heteroaromatic sulfonamide wherein a mixed sulfonic acid anhydride synthesized from a heteroaromatic ring sulfonic acid compound and a perfluoroalkyl sulfonic acid anhydride or a perfluoroalkyl sulfonic acid halide is reacted with amine, thereby the reaction proceeds in a small amount of time and with good selectivity, and fewer side reactions occur, thus leading to the present invention.

Means for Solving the Problems

That is, the present invention relates to:
1) a method for producing a mixed sulfonic acid anhydride of the general formula (1):

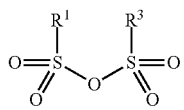
(1)

wherein
$R^1$ is a heteroaryl group which may have a substituent; and
$R^3$ is a perfluoroalkyl group, comprising:
reacting a sulfonic acid compound of the general formula (2):

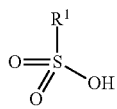
(2)

wherein
$R^1$ is as defined above,
with a sulfonylating agent selected from the group consisting of a perfluoroalkyl sulfonic acid anhydride and a perfluoroalkyl sulfonic acid halide;

2) a method for producing a sulfonamide compound of the general formula (4):

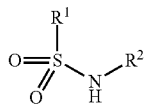
(4)

wherein
$R^1$ is as defined above; and
$R^2$ is an alkyl group, an alkenyl group, an alkynyl group, a cycloalkyl group, an aryl group, a heteroaryl group, an aralkyl group or a heteroarylalkyl group which may have a substituent,
comprising:
reacting an amine compound of the general formula (3):

  $H_2N-R^2$ (3)

wherein
$R^2$ is as defined above,
with the mixed sulfonic acid anhydride of the general formula (1); and 3) a method for producing a sulfonamide compound of the general formula (4):

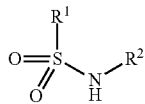
(4)

wherein
$R^1$ is a heteroaryl group which may have a substituent; and
$R^2$ is an alkyl group, an alkenyl group, an alkynyl group, a cycloalkyl group, an aryl group, a heteroaryl group, an aralkyl group or a heteroarylalkyl group, which may have a substituent, comprising the steps of:

(A) reacting a sulfonic acid compound of the general formula (2):

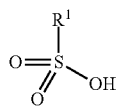
(2)

wherein
$R^1$ is as defined above,
with a sulfonylating agent selected from the group consisting of a perfluoroalkyl sulfonic acid anhydride or a perfluoroalkyl sulfonic acid halide; and
(B) subsequently conducting a reaction by adding an amine compound of the general formula (3):

 $H_2N-R^2$ (3)

wherein
$R^2$ is as defined above,
to the reaction solution obtained in the step (A).

In addition, the present invention provides a mixed sulfonic acid anhydride of the general formula (1):

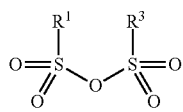
(1)

wherein
$R^1$ and $R^3$ are as defined above.

Effect of the Invention

According to the present invention, a high-purity sulfonamide compound of the general formula (4) can be produced with a high yield and good selectivity, from a heteroaromatic sulfonic acid compound of the general formula (2) and an amine compound of the general formula (3), by a convenient and industrially preferred method under mild conditions.

MODE FOR CARRYING OUT THE INVENTION

The heteroaromatic sulfonamide compound of the general formula (4) of the present invention can be obtained by synthesizing a mixed sulfonic acid anhydride of the general formula (1) in the presence of a base from heteroaromatic sulfonic acid of the general formula (2) and a perfluoroalkyl sulfonic acid anhydride or a perfluoroalkyl sulfonic acid halide (Reaction A) and subsequently reacting the resulting mixed sulfonic acid anhydride with amine of the general formula (4) (Reaction B) (see [Reaction formula I] below; only example using perfluoroalkyl sulfonic acid anhydride is shown.).

[Reaction formula I]

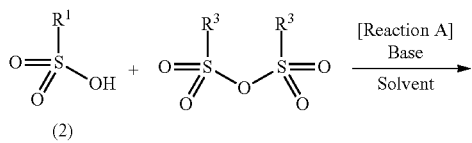

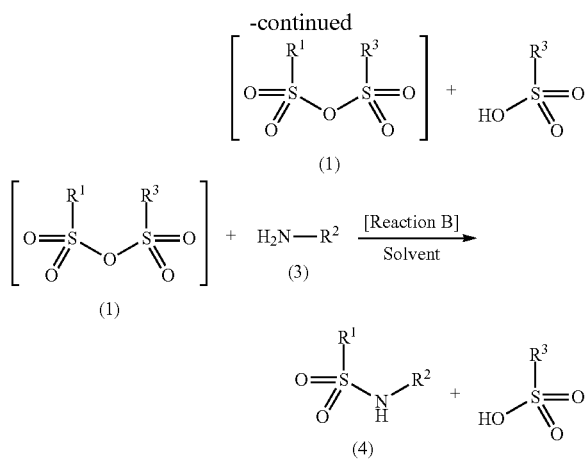

wherein
R² and R³ are as defined above.

In the present invention, the following terms, alone or in combination with other terms, have the meanings given below, unless otherwise stated.

"Alkyl group" means a monovalent group of linear or branched, saturated aliphatic hydrocarbon. Typical examples include an alkyl group having 1 to 10 carbon atoms, for example, a methyl group, an ethyl group, a propyl group, a butyl group, a pentyl group, a hexyl group, a heptyl group, an octyl group, a nonyl group or a decyl group (including various isomers). Preferred examples include an alkyl group having 1 to 6 carbon atoms, for example, a methyl group, an ethyl group, a propyl group, an isopropyl group, a butyl group, an isobutyl group or a hexyl group, and more preferred examples include an alkyl group having 1 to 4 carbon atoms, for example, a methyl group, an ethyl group, a propyl group, an isopropyl group, a butyl group or an isobutyl group.

The "perfluoroalkyl" moiety of "perfluoroalkyl group" and "perfluoroalkyl sulfonic acid" means an alkyl group wherein all hydrogen atoms of the "alkyl group" defined above are replaced with fluorine atoms. Typical examples include a perfluoroalkyl group having 1 to 6 carbon atoms, for example, a trifluoromethyl group, a pentafluoroethyl group (perfluoroethyl group), a heptafluoropropyl group (perfluoropropyl group), a nonafluorobutyl group (perfluorobutyl group), an undecafluoropentyl group (perfluoropentyl group), and tridecafluorohexyl group (perfluorohexyl group) (including various isomers). Preferred example is a perfluoroalkyl group having 1 to 4 carbon atoms, for example, a trifluoromethyl group, a pentafluoroethyl group, a heptafluoropropyl group, or a nonafluorobutyl group, and more preferred example is a trifluoromethyl group.

"Alkenyl group" means a monovalent group of linear or branched, unsaturated aliphatic hydrocarbon which includes at least one carbon-carbon double bond. Typical examples include an alkenyl group having 2 to 10 carbon atoms, for example, a vinyl group, a propenyl group, a butenyl group, a pentenyl group, a hexenyl group, a heptenyl group, an octenyl group, a nonenyl group or a decenyl group (including various isomers). Preferred example is an alkenyl group having 2 to 6 carbon atoms, for example, a vinyl group, a propenyl group, a butenyl group, a pentenyl group or a hexenyl group, and more preferred example is an alkenyl group having 2 to 4 carbon atoms, for example, a vinyl group, a 1-propenyl group, a 2-propenyl group, a 1-butenyl group or a 2-butenyl group.

"Alkynyl group" means a monovalent group of linear or branched, unsaturated aliphatic hydrocarbon which includes at least one carbon-carbon triple bond. Typical examples include an alkynyl group having 2 to 10 carbon atoms, for example, an ethynyl group, a propynyl group, a butynyl group, a pentynyl group, a hexynyl group, a heptynyl group, an octynyl group, a nonynyl group or a decynyl group (including various isomers). Preferred example is an alkynyl group having 2 to 6 carbon atoms, for example, an ethynyl group, a propynyl group, a butynyl group, a pentynyl group or a hexynyl group, and more preferred example is an alkynyl group having 2 to 4 carbon atoms, for example, an ethynyl group, a 2-propynyl group, a 3-butynyl group or a 2-butynyl group.

"Cycloalkyl group" means a monovalent group of cyclic saturated aliphatic hydrocarbon. Typical examples include a cycloalkyl group having 3 to 10 carbon atoms, for example, a cyclopropyl group, a cyclobutyl group, a cyclopentyl group, a cyclohexyl group, a cycloheptyl group, a cyclooctyl group, a cyclononyl group or a cyclodecyl group. Preferred example is a cycloalkyl group having 3 to 8 carbon atoms, for example, a cyclopropyl group, a cyclobutyl group, a cyclopentyl group, a cyclohexyl group, a cycloheptyl group or a cyclooctyl group, and more preferred example is a cycloalkyl group having 3 to 6 carbon atoms, for example, a cyclopropyl group, a cyclobutyl group, a cyclopentyl group or a cyclohexyl group.

"Aryl group" means a monovalent group of monocyclic or condensed polycyclic aromatic hydrocarbon. Typical examples include an aryl group having 6 to 14 carbon atoms, for example, a phenyl group, a naphthyl group or an anthryl group, and preferred example is an aryl group having 6 to 10 carbon atoms, for example, a phenyl group, a 1-naphthyl group or a 2-naphthyl group.

"Heteroaryl group" means a monovalent group of a monocyclic or condensed polycyclic aromatic heterocyclic compound, which includes at least one hetero atom selected from the group consisting of a nitrogen atom, an oxygen atom and a sulfur atom. Typical examples include a 5 to 10 membered heteroaryl group, for example, a pyrrolyl group, an imidazolyl group, a pyrazolyl group, a triazolyl group, a pyridyl group, a pyrimidinyl group, a pyridazinyl group, an indolyl group, a quinolyl group; a thienyl group, a benzothienyl group; a furyl group, a benzofuranyl group; an oxazolyl group, an isoxazolyl group, a thiazolyl group, an isothiazolyl group, an oxadiazolyl group, and a thiadiazolyl group (including various isomers). Preferred example is a 5 to 6 membered heteroaryl group, for example, a 2-pyrrolyl group, a 3-pyrrolyl group, a 1-pyrazolyl group, a 1,2,4-triazol-1-yl group, a 2-pyridyl group, a 3-pyridyl group, a 4-pyridyl group, a 2-pyrimidinyl group, a 4-pyridazinyl group, a 2-thienyl group, a 3-thienyl group, a 2-furyl group, a 3-furyl group, a 2-thiazolyl group or a 4-thiazolyl group.

"Aralkyl group" means an alkyl group substituted with an aryl group. Here, "aryl group" and "alkyl group" are as defined above. Typical examples include an aralkyl group having 7 to 14 carbon atoms, for example, a benzyl group, a phenethyl group, a phenylpropyl group, a phenylbutyl group, a naphthylmethyl group or a naphthylethyl group (including various isomers), and preferred example is an aralkyl group having 7 to 10 carbon atoms, for example, a benzyl group, a 1-phenethyl group, a 2-phenethyl group, a 3-phenylpropyl group or a 4-phenylbutyl group.

"Heteroarylalkyl group" means an alkyl group substituted with a heteroaryl group. Here, "heteroaryl group" and "alkyl group" are as defined above. Typical examples include a 6 to 14 membered heteroarylalkyl group, for example, a pyrrolylmethyl group, a pyrrolylethyl group, an imidazolylmethyl group, an imidazolylethyl group, a pyrazolylmethyl group, a pyrazolylethyl group, a triazolylmethyl group, a triazolylethyl group, a pyridylmethyl group, a pyridylethyl group, a pyrimidinylmethyl group, a pyrimidinylethyl group, a pyridazinylmethyl group, a pyridazinylethyl group, an indolylmethyl group, an indolylethyl group, a quinolylmethyl group, a quinolylmethylethyl group; a thienylmethyl group, a thienylethyl group, a benzothienylmethyl group, a benzothienylethyl group; a furylmethyl group, a furylethyl group, a benzofuranylmethyl group, a benzofuranylethyl group; an oxazolylmethyl group, an oxazolylethyl group, an isoxazolylmethyl group, an isoxazolylethyl group, a thiazolylmethyl group, a thiazolylethyl group, an isothiazolylmethyl group, an isothiazolylethyl group, an oxadiazolylmethyl group, an oxadiazolylethyl group, a thiadiazolylmethyl group, and a thiadiazolylethyl group (including various isomers). Preferred example is a 6 to 10 membered heteroarylalkyl group, for example, a 2-pyridylmethyl group, a 3-pyridylmethyl group, a 2-pyrimidinylmethyl group, a 5-pyrimidinylmethyl group, a 2-indolylmethyl group, a 5-indolylmethyl group, a 2-benzofuranylmethyl group, a 5-indolylmethyl group, a 2-benzothienylmethyl group or a 5-benzothienylmethyl group.

"Halide" of "perfluoroalkyl sulfonic acid halide" and the like means a halogen atom, which is, for example, a fluorine atom, a chlorine atom, a bromine atom or an iodine atom, preferably a chlorine atom or a bromine atom, and more preferably a chlorine atom.

In the general formulae (1), (2), and (4), $R^1$ indicates a heteroaryl group which may have a substituent.

A "group which may have a substituent" in the present invention means, unless otherwise stated, to include both instances where the group has at least one substituent and where the group has no substituent (that is, when it is unsubstituted). For example, "a heteroaryl group which may have a substituent" is "a heteroaryl group having no substituent" or "a heteroaryl group having a substituent(s)".

In a preferred embodiment of the present invention, $R^1$ in the general formula (1) is a pyridyl group which may have a substituent.

"A heteroaryl group (particularly, a pyridyl group) which may have a substituent" in $R^1$ is preferably a 5 to 10 membered heteroaryl group (particularly, a pyridyl group); or a 5 to 10 membered heteroaryl group (particularly, a pyridyl group) substituted with one, two or three substituents selected from the group consisting of a halogen atom, a hydroxy group, an alkyl group having 1 to 4 carbon atoms, an alkoxy group having 1 to 4 carbon atoms, an amino group, a cyano group and a nitro group. Two or more substituents may be the same or different.

In the present invention, "halogen atom" or "halo" means a fluorine atom, a chlorine atom, a bromine atom or an iodine atom. Preferred example is a fluorine atom, a chlorine atom or a bromine atom, more preferred example is a fluorine atom or a chlorine atom, and particularly preferred example is a fluorine atom.

"Alkoxy group having 1 to 4 carbon atoms" in the present invention means a group —OR (wherein R is an alkyl group having 1 to 4 carbon atoms as defined above). Examples of an alkoxy group having 1 to 4 carbon atoms include a methoxy group, an ethoxy group, a propyloxy group, an isopropyloxy group, a butyloxy group or an isobutyloxy group.

"Heteroaryl group which has no substituent" includes, for example, a heteroaryl group such as a 2-furyl group, a 3-furyl group, a 2-pyridyl group, a 3-pyridyl group, a 4-pyridyl group, a 2-pyrrolyl group, a 3-pyrrolyl group, a 2-thienyl group, a 3-thienyl group, a 2-indolyl group, a 3-indolyl group, a 2-imidazolyl group, a 4-imidazolyl group, a 3-pyrazolyl group, a 2-pyrimidinyl group, a 4-pyrimidinyl group or a quinolyl group (these groups include various isomers.), and preferred example is a 2-pyridyl group, a 3-pyridyl group or a 4-pyridyl group.

"Heteroaryl group which has a substituent" includes, for example, a 2-(3-methyl)furyl group, a 2-(4-methyl)furyl group, a 2-(3-ethyl)furyl group, a 2-(4-ethyl)furyl group, a 2-(3-fluoro)furyl group, a 2-(3-chloro)furyl group, a 2-(3-hydroxy)furyl group, a 2-(3-methoxy)furyl group, a 2-(3-amino)furyl group, a 2-(3-nitro)furyl group, a 2-(3-cyano)furyl group, a 2-(3-methyl)pyridyl group, a 2-(4-methyl)pyridyl group, a 2-(3-ethyl)pyridyl group, a 2-(4-ethyl)pyridyl group, a 2-(3-fluoro)pyridyl group, a 2-(4-chloro)pyridyl group, a 2-(3-hydroxy)pyridyl group, a 2-(3-methoxy)pyridyl group, a 2-(3-amino)pyridyl group, a 2-(3-nitro)pyridyl group, a 2-(3-cyano)pyridyl group, a 2-(3,5-dichloro)pyridyl group, a 3-(2-chloro)pyridyl group, a 2-(3-methyl)pyrrolyl group or a 2-(3-methyl)thienyl group, and preferred example is a 2-(3-methyl)furyl group, a 2-(3-fluoro)furyl group, a 2-(3-methyl)pyridyl group, a 2-(3-fluoro)pyridyl group, a 2-(3-nitro)pyridyl group, a 2-(3-cyano)pyridyl group or a 2-(3,5-dichloro)pyridyl group.

In the general formulae (3) and (4), $R^2$ is an alkyl group, an alkenyl group, an alkynyl group, a cycloalkyl group, an aryl group, a heteroaryl group, an aralkyl group or a heteroarylalkyl group which may have a substituent.

Examples of a substituent of "alkyl group which may have a substituent", "alkenyl group which may have a substituent", "alkynyl group which may have a substituent" or "cycloalkyl group which may have a substituent" in $R^2$ include a halogen atom; a hydroxy group; an alkoxy group having 1 to 10 carbon atoms; an amino group which may have a substituent; a cyano group; or a nitro group. Two or more substituents may be the same or different.

Examples of a substituent of "aryl group which may have a substituent", "heteroaryl group which may have a substituent", "aralkyl group which may have a substituent" or "heteroarylalkyl group which may have a substituent" in $R^2$ include a halogen atom; an alkyl group having 1 to 10 carbon atoms; an alkenyl group having 2 to 10 carbon atoms; an alkynyl group having 2 to 10 carbon atoms; an aryl group which may have a substituent; a heteroaryl group which may have a substituent; an aralkyl group which may have a substituent; a heteroarylalkyl group which may have a substituent; an alkoxy group having 1 to 10 carbon atoms; an alkoxyalkoxy group having 2 to 20 carbon atoms; an acyl group having 2 to 11 carbon atoms; an alkoxycarbonyl group having 2 to 11 carbon atoms; an alkoxycarbonylalkyl group having 3 to 21 carbon atoms; an alkoxycarbonylalkoxy group having 3 to 21 carbon atoms; an aryloxy group having 6 to 14 carbon atoms; an aralkyloxy group having 7 to 14 carbon atoms; a haloalkyl group having 1 to 4 carbon atoms; an amino group which may have a substituent; a cyano group; or a nitro group. Two or more substituents may be the same or different. Further, two substituents which are attached to adjacent ring atoms may form a ring together with the ring atoms.

Examples of a substituent of "aryl group which may have a substituent", "heteroaryl group which may have a substituent", "aralkyl group which may have a substituent" or "heteroarylalkyl group which may have a substituent" in examples of a substituent as described above include a halogen atom; an alkyl group having 1 to 10 carbon atoms; an alkenyl group having 2 to 10 carbon atoms; an alkynyl group having 2 to 10 carbon atoms; an alkoxy group having 1 to 10 carbon atoms; a haloalkyl group having 1 to 4 carbon atoms; a cyano group; or a nitro group. Two or more substituents may be the same or different.

"Alkoxy group having 1 to 10 carbon atoms" in the present invention means a group —OR (wherein R is an alkyl group having 1 to 10 carbon atoms as defined above). Examples of an alkoxy group having 1 to 10 carbon atoms include a methoxy group, an ethoxy group, a propoxy group, a butoxy group, a pentyloxy group, a hexyloxy group, a heptyloxy group, an octyloxy group, a nonyloxy group or a decyloxy group (including various isomers). Preferred example is an alkoxy group having 1 to 6 carbon atoms, for example, a methoxy group, an ethoxy group, a propyloxy group, an isopropyloxy group, a butyloxy group, an isobutyloxy group or a hexyloxy group, and more preferred example is an alkoxy group having 1 to 4 carbon atoms, for example, a methoxy group, an ethoxy group, a propyloxy group, an isopropyloxy group, a butyloxy group or an isobutyloxy group.

Similarly, "alkoxyalkoxy group having 2 to 20 carbon atoms" means an alkoxy group having 1 to 10 carbon atoms and substituted with an alkoxy group having 1 to 10 carbon atoms. Here, "alkoxy group having 1 to 10 carbon atoms" is as defined above. Preferable example is an alkoxyalkoxy group having 2 to 8 carbon atoms, and more preferred example is an alkoxyalkoxy group having 2 to 4 carbon atoms, for example, a methoxymethoxy group, a methoxyethoxy group, an ethoxymethoxy group or an ethoxyethoxy group.

Similarly, "acyl group having 2 to 11 carbon atoms" means a group —C(=O)—R (wherein R is an alkyl group having 1 to 10 carbon atoms as defined above). Examples of an acyl group having 2 to 11 carbon atoms include an acetyl group, a propionyl group, a butyryl group, a valeryl group, a hexanoyl group, an octanoyl group or a decanoyl group (including various isomers). Preferred example is an alkoxycarbonyl group having 2 to 7 carbon atoms, and more preferred example is an alkoxycarbonyl group having 2 to 5 carbon atoms, for example, an acetyl group, a propionyl group, a butyryl group, an isobutyryl group, a valeryl group, an isovaleryl group or a pivaloyl group.

Similarly, "alkoxycarbonyl group having 2 to 11 carbon atoms" means a group —C(=O)—OR (wherein R is an alkyl group having 1 to 10 carbon atoms as defined above). Examples of an alkoxycarbonyl group having 2 to 11 carbon atoms include a methoxycarbonyl group, an ethoxycarbonyl group, a propoxycarbonyl group, a butoxycarbonyl group, a pentyloxycarbonyl group, a hexyloxycarbonyl group, a heptyloxycarbonyl group, an octyloxycarbonyl group, a nonyloxycarbonyl group or a decyloxycarbonyl group (including various isomers). Preferred example is an alkoxycarbonyl group having 2 to 7 carbon atoms, for example, a methoxycarbonyl group, an ethoxycarbonyl group, a propoxycarbonyl group, an isopropoxycarbonyl group, a butoxycarbonyl group, a tert-butoxycarbonyl group or a hexyloxy group, and more preferred example is an alkoxycarbonyl group having 2 to 5 carbon atoms, for example, a methoxycarbonyl group, an ethoxycarbonyl group, a propoxycarbonyl group, an isopropoxycarbonyl group, a butoxycarbonyl group or a tert-butoxycarbonyl group.

Similarly, "alkoxycarbonylalkyl group having 3 to 21 carbon atoms" means an alkyl group having 1 to 10 carbon atoms and substituted with an alkoxycarbonyl group having 2 to 11 carbon atoms. Here, "alkoxycarbonyl group having 2 to 11 carbon atoms" and "alkyl group having 1 to 10 carbon atoms" are as defined above. Preferred example is an alkoxycarbonylalkyl group having 3 to 11 carbon atoms, and more preferred example is an alkyl group having 1 to 4 carbon atoms and substituted with an alkoxycarbonyl group having 2 to 5 carbon atoms (namely, an alkoxycarbonylalkyl group having 3 to 9 carbon atoms), for example, a methoxycarbonylmethyl group, an ethoxycarbonylmethyl group, a propoxycarbonylmethyl group, an isopropoxycarbonylmethyl group, a butoxycarbonylmethyl group, a tert-butoxycarbonylmethyl group, a methoxycarbonylethyl group, an ethoxycarbonylethyl group, a propoxycarbonylethyl group, an isopropoxycarbonylethyl group, a butoxycarbonylethyl group or a tert-butoxycarbonylethyl group.

Similarly, "alkoxycarbonylalkoxy group having 3 to 21 carbon atoms" means an alkoxy group having 1 to 10 carbon atoms and substituted with an alkoxycarbonyl group having 2 to 11 carbon atoms. Here, "alkoxycarbonyl group having 2 to 11 carbon atoms" and "alkoxy group having 1 to 10 carbon atoms" are as defined above. Preferred example is an alkoxycarbonylalkoxy group having 3 to 11 carbon atoms, and more preferred example is an alkoxy group having 1 to 4 carbon atoms and substituted with an alkoxycarbonyl group having 2 to 5 carbon atoms (namely, an alkoxycarbonylalkoxy group having 3 to 9 carbon atoms), for example, a methoxycarbonylmethoxy group, an ethoxycarbonylmethoxy group, a propoxycarbonylmethoxy group, an isopropoxycarbonylmethoxy group, an butoxycarbonylmethoxy group, a tert-butoxycarbonylmethoxy group, a methoxycarbonylethoxy group, an ethoxycarbonylethoxy group, a propoxycarbonylethoxy group, an isopropoxycarbonylethoxy group, a butoxycarbonylethoxy group or a tert-butoxycarbonylethoxy group.

Similarly, "aryloxy group having 6 to 14 carbon atoms" means a group —OR' (wherein R' is aryl having 6 to 14 carbon atoms as defined above). Examples of an aryloxy group having 6 to 14 carbon atoms include a phenoxy group, a naphthyloxy group or an anthryloxy group. Preferred example is an aryloxy group having 6 to 10 carbon atoms, for example, a phenoxy group, a 1-naphthyloxy group or a 2-naphthyloxy group.

Similarly, "aralkyloxy group having 7 to 14 carbon atoms" means a group —OR" (wherein R" is an aralkyl group as defined above). Typical examples include an aralkyloxy group having 7 to 14 carbon atoms, for example, a benzyloxy group, a phenethyloxy group, a phenylpropyloxy group, a phenylbutyloxy group, a naphthylmethyloxy group or a naphthylethyloxy group (including various isomers). Preferred example is an aralkyloxy group having 7 to 10 carbon atoms, for example, a benzyloxy group, a 1-phenethyloxy group, a 2-phenethyloxy group, a 3-phenylpropyloxy group or a 3-phenylbutyloxy group.

Similarly, "haloalkyl group having 1 to 4 carbon atoms" means an alkyl group having 1 to 4 carbon atoms and substituted with one or more halogen atoms. Here, "halo" and "alkyl group having 1 to 4 carbon atoms" are as defined above. Examples of a haloalkyl group having 1 to 4 carbon atoms include a fluoromethyl group, a difluoromethyl group, a trifluoromethyl group, a 2-fluoroethyl group, a 2,2-difluoroethyl group, a 2,2,2-trifluoroethyl group, a pentafluoroethyl group or a nonafluorobutyl group. Preferred example is a fluoroalkyl group having 1 to 2 carbon atoms, for example, a fluoromethyl group, a difluoromethyl group, a trifluoromethyl group, a 2-fluoroethyl group, a 2,2-difluoroethyl group, a 2,2,2-trifluoroethyl group or a pentafluoroethyl group.

"Amino group which may have a substituent" in examples of a substituent as described above means an amino group or an amino group having one or two substituents. Examples of the substituents include an alkyl group having 1 to 10 carbon atoms; an alkoxycarbonylalkyl group having 3 to 20 carbon atoms; or an acyl group having 2 to 10 carbon atoms. Two substituents may be the same or different.

In a preferred embodiment of the present invention, $R^2$ in the general formulae (1), (3), and (4) is an aralkyl group which may have a substituent. In a particularly preferred embodiment of the present invention, $R^2$ in the general formulae (1), (3), and (4) is a benzyl group which may have a substituent.

Examples of "aralkyl group (particularly, benzyl group) which may have a substituent" in $R^2$ include an aralkyl group (particularly, benzyl group); or an aralkyl group (particularly, benzyl group) substituted with one, two or three substituents selected from the group consisting of a halogen atom, an alkyl group having 1 to 10 carbon atoms, an alkenyl group having 2 to 10 carbon atoms, an alkynyl group having 2 to 10 carbon atoms, an aryl group which may have a substituent, a heteroaryl group which may have a substituent, an aralkyl group which may have a substituent, a heteroarylalkyl group which may have a substituent, an alkoxy group having 1 to 10 carbon atoms, an alkoxyalkoxy group having 2 to 20 carbon atoms, an aryloxy group having 6 to 14 carbon atoms, an aralkyloxy group having 7 to 14 carbon atoms, a haloalkyl group having 1 to 4 carbon atoms, a cyano group, and a nitro group. Here, two or more substituents may be the same or different. Further, two substituents which are attached to adjacent ring atoms may form a ring together with the ring atoms.

"Aralkyl group (particularly, benzyl group) which may have a substituent" in $R^2$ is preferably an aralkyl group (particularly, benzyl group) having 7 to 10 carbon atoms; or an aralkyl group (particularly, benzyl group) having 7 to 10 carbon atoms and substituted with one, two or three substituents selected from the group consisting of a halogen atom, an alkyl group having 1 to 4 carbon atoms, an aryl group which may have a substituent, a heteroaryl group which may have a substituent, an alkoxy group having 1 to 4 carbon atoms, an alkoxyalkoxy group having 2 to 4 carbon atoms, an aryloxy group having 6 to 10 carbon atoms, an aralkyloxy group having 7 to 10 carbon atoms, a haloalkyl group having 1 to 4 carbon atoms, a cyano group, and a nitro group. Two or more substituents may be the same or different.

"Aralkyl group (particularly, benzyl group) which may have a substituent" in $R^2$ is more preferably an aralkyl group (particularly, benzyl group) having 7 to 10 carbon atoms; or an aralkyl group (particularly, benzyl group) having 7 to 10 carbon atoms and substituted with an aryl group which may have a substituent or a heteroaryl group which may have a substituent.

Aralkyl group which may have a substituent in $R^2$ is further preferably a benzyl group, a phenethyl group, a 3-phenylpropyl group or a 4-phenylbutyl group; a biphenyl-4-ylmethyl group, a 2'-ethoxybiphenyl-4-ylmethyl group, a 3'-ethoxybiphenyl-4-ylmethyl group, a 4'-ethoxybiphenyl-4-ylmethyl group, a 2'-(1-propenyl)biphenyl-4-ylmethyl group, a 2'-(1-propenyl)biphenyl-4-ylmethyl group, a 3'-(1-propenyl)biphenyl-4-ylmethyl group, a 4'-(1-propenyl)biphenyl-4-ylmethyl group, a 2'-(1-propynyl)biphenyl-4-ylmethyl group, a 3'-(1-propynyl)biphenyl-4-ylmethyl group or a 4'-(1-propynyl)biphenyl-4-ylmethyl group; a 4-(thiazol-2-yl)benzyl group, a 3-(thiazol-2-yl)benzyl group, a 2-(thiazol-2-yl)benzyl group, a 4-(thiazol-4-yl)benzyl group, a 4-(4-methylthiazol-2-yl)benzyl group, a 4-(5-methylthiazol-2-yl)benzyl group, a 4-(4,5-dimethylthiazol-2-yl)benzyl group, a 4-(5-fluorothiazol-2-yl)benzyl group, a 4-(5-chlorothiazol-2-yl)benzyl group, a 4-(4-trifluoromethylthiazol-2-yl)benzyl group, a 4-(5-trifluoromethylmethylthiazol-2-yl)benzyl group, a 4-((1H-1)-pyrazol-1-yl)benzyl group, a 3-((1H)-pyrazol-1-yl)benzyl group, a 2-((1H)-pyrazol-1-yl) benzyl group, a 4-(3-methyl-(1H)-pyrazol-1-yl)benzyl group, a 4-(5-methyl-(1H)-pyrazol-1-yl)benzyl group, a 4-(oxazol-1-yl)benzyl group, a 3-(oxazol-1-yl)benzyl group, a 2-(oxazol-1-yl)benzyl group, a 4-(5-methyloxazol-1-yl) benzyl group or a 4-(4-methyloxazol-1-yl)benzyl group.

Examples of "perfluoroalkyl group" in $R^3$ include a perfluoroalkyl group having 1 to 6 carbon atoms, for example, a trifluoromethyl group, a pentafluoroethyl group, a heptafluoropropyl group, a nonafluorobutyl group, an undecafluoropentyl group, a tridecafluorohexyl group (including various isomers). Preferred example is a perfluoroalkyl group having 1 to 4 carbon atoms, for example, a trifluoromethyl group, a pentafluoroethyl group, a heptafluoropropyl group, or a nonafluorobutyl group, more preferred example is a trifluoromethyl group or a nonafluorobutyl group, and particularly preferred example is a trifluoromethyl group.

In a preferred embodiment of the present invention, the amine compound of the general formula (3) is an amine compound of the general formula (5):

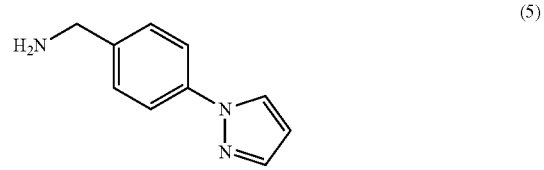

The present invention is carried out by a method comprising the steps of: reacting a perfluoroalkyl sulfonic acid anhydride or a perfluoroalkyl sulfonic acid halide with a heteroaromatic sulfonic acid compound of the general formula (2) in the presence or absence of an organic solvent and in the presence or absence of a base to synthesize a mixed sulfonic acid anhydride (1) (Reaction A); and subsequently reacting the resulting mixed sulfonic acid anhydride (1) with an amine compound of the general formula (3) to synthesize a sulfonamide compound (4) (Reaction B). The mixed sulfonic acid anhydride (1) obtained by Reaction A can be used in Reaction B without isolation.

The heteroaromatic sulfonic acid compound of the general formula (2) used in the present invention may be a commercially available product, or can be synthesized by a known method. The heteroaromatic sulfonic acid compound used in the present invention is, for example, pyridine-2-sulfonic acid, pyridine-3-sulfonic acid, pyridine-4-sulfonic acid, 4-methylpyridine-2-sulfonic acid, 1H-pyrrole-2-sulfonic acid, thiophene-2-sulfonic acid, thiophene-3-sulfonic acid, furan-2-sulfonic acid or furan-3-sulfonic acid, and commercially available products were used in Examples.

For the use in the present invention, commercially available perfluoroalkyl sulfonic acid anhydrides or perfluoroalkyl sulfonic acid halides are good enough, but those having a purity of 95% or more are preferable, and those having a purity of 98% or more are more preferable. The perfluoroalkyl sulfonic acid anhydride used in the present invention is, for example, a trifluoromethanesulfonic acid anhydride, a pentafluoroethanesulfonic acid anhydride, a heptafluoropropanesulfonic acid anhydride, or a nonafluorobutanesulfonic acid anhydride, and a perfluoroalkyl sulfonic acid halide used in the present invention is, for example, a trifluoromethanesulfonic acid chloride, a pentafluoroethanesulfonic acid chloride, a heptafluoropropanesulfonic acid chloride, or a nonafluorobutanesulfonic acid chloride, and commercially available products were used in Examples.

The amount of a perfluoroalkyl sulfonic acid anhydride or a perfluoroalkyl sulfonic acid halide to be used is, for example, 0.5 to 10 mol, preferably 0.5 to 5 mol, more preferably 0.8 to 2 mol, and particularly preferably 0.8 to 1.5 mol per mole of a heteroaromatic sulfonic acid compound of the general formula (2).

The reaction of the present invention (Reaction A) can be carried out in the presence of a base. Any base can be used in the reaction of the present invention as long as it does not affect the reaction. Such base is, for example, an aliphatic amine such as triethylamine, tributylamine or diisopropylethylamine, or an aromatic amine such as pyridine or N,N-dimethyl-4-aminopyridine, and is preferably an aromatic amine and more preferably pyridine or N,N-dimethyl-4-aminopyridine.

The amount of a base to be used is, for example, 0.01 to 10 mol, preferably 0.05 to 5 mol, and more preferably 0.1 to 2 mol per mole of a heteroaromatic sulfonic acid compound of the general formula (2). In addition, when the base is pyridine etc., a large amount of it can be used as a solvent.

The reaction of the present invention (Reaction B) does not particularly require any bases. However, when a mixed sulfonic acid anhydride is synthesized in Reaction A and then Reaction B is directly carried out in the system, the base having been used in Reaction A can remain as it is.

The reaction of the present invention (Reaction A) can be carried out in the presence of an organic solvent. Any organic solvent can be used in the reaction of the present invention as long as it does not participate in the reaction. Such organic solvent includes, for example, nitrile-based organic solvents such as acetonitrile or benzonitrile; amide-based solvents such as N,N-dimethylformamide, N,N-dimethylacetamide, N-methylpyridone, dimethylimidazole or 1,3-dimethyl-2-imidazolidinone; halogen-based organic solvents such as methylene chloride, chloroform or 1,2-dichloroethane; aliphatic hydrocarbon-based solvents such as n-pentane, n-hexane, n-heptane, n-octane, cyclopentane, cyclohexane or cyclopentane; aromatic hydrocarbon-based solvents such as benzene, toluene or xylene; ether-based solvents such as diethylether, tert-butylmethyl ether, diisopropyl ether, THF or 1,4-dioxane; or aromatic amine-based solvents which can be used as a base in the present invention, for example, pyridine, is preferably an aromatic hydrocarbon-based organic solvent, a halogen-based organic solvent, a nitrile-based organic solvent or an aromatic amine-based solvents, more preferably a halogen-based organic solvent, a nitrile-based organic solvent or an aromatic amine-based solvent, and particularly preferably methylene chloride, acetonitrile or pyridine. Further, these organic solvents may be used alone or in combination of two or more of them.

The amount of an organic solvent to be used is, for example, 1 to 200 mL, preferably 2 to 100 mL, and more preferably 5 to 50 mL per gram of a heteroaromatic sulfonic acid compound of the general formula (1).

The reaction of the present invention (Reaction B) can be carried out in the presence of an organic solvent. Any organic solvent can be used in the reaction of the present invention as long as it does not participate in the reaction. Such organic solvent includes the same organic solvents as Reaction A. In addition, when a mixed sulfonic acid anhydride is synthesized in Reaction A and then Reaction B is directly carried out in the system, the organic solvent having been used in Reaction A can be used as it is, or the organic solvent may be freshly added.

An amine compound of the general formula (3) used in the present invention may be a commercially available product, or can be synthesized by a known method. For example, amine compounds described in Examples of the present invention can be synthesized by a method disclosed in Patent Document 1.

The amount of the amine compound to be used is, for example, 0.5 to 10 mol, preferably 0.8 to 5 mol, and more preferably 0.9 to 2 mol per mole of a heteroaromatic sulfonic acid compound of the general formula (2).

The reaction temperature in the reactions of the present invention (Reactions A and B) is, for example, from −20 to 200° C., preferably from 0 to 100° C., and more preferably from 10 to 80° C.

The reaction pressure in the reactions of the present invention (Reactions A and B) is not particularly limited, but it is preferable to carry out the reactions under normal pressure.

The production equipment for the present invention is not particularly limited, and general production equipment, for example, a reaction vessel, a heating (cooling) device, a distillation device (for example, Dean-Stark trap), etc. can be used.

Further, a heteroaromatic sulfonamide compound of the general formula (3) obtained by a method of the present invention can be further purified by a general method such as distillation, phase separation, extraction, crystallization, recrystallization and column chromatography.

EXAMPLES

The present invention is specifically explained below, by presenting examples, but the scope of the present invention is not limited thereto.

The structure confirmation of the desired compounds obtained was conducted by IR, NMR spectral analysis, etc. Further, the reaction yields (internal standard method) and the chemical purities were measured by using high-performance liquid chromatography (HPLC).

Example 1

Synthesis of N-[4-(1H-pyrazol-1-yl)benzyl]pyridine-3-sulfonamide

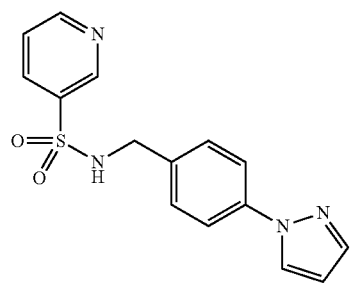 [SMILES: O=S(=O)(NCc1ccc(-n2cccn2)cc1)c1cccnc1]

In a glass vessel having an internal volume of approximately 2 L and equipped with a stirrer and a thermometer, 900 mL of pyridine, 60.0 g of pyridine-3-sulfonic acid (0.377 mol, Wako Pure Chemical Industries, Ltd.), and 5.99 g (0.049 mol) of N,N-dimethyl-4-aminopyridine were mixed, 104 g of trifluoromethanesulfonic acid anhydride with a purity of 98% or more (0.369 mol, Tokyo Chemical Industry Co., Ltd.) was added dropwise at room temperature with stirring, and the mixture was stirred at 30° C. for 1 hour. Subsequently, 76.7 g (0.366 mmol) of 4-(1H-pyrazol-1-yl) benzylamine hydrochloride synthesized by a method similar to that described in Reference Example 2 was added portionwise to the reaction mixture at the same temperature, and the mixture was stirred at 30° C. for 1 hour. After completion of the reaction, the reaction mixture was concentrated under reduced pressure, and to the residue were added 1500 mL of ethyl acetate and 1260 mL of water to separate the layers. The resulting organic layer was separated into two parts, each of the parts was washed sequentially with a saturated aqueous ammonium chloride solution and 600 mL of water, and the organic layers were combined and concentrated under reduced pressure. To the resulting residue was added 630 mL of diisopropyl ether, and the mixture was stirred at 0° C. for 1 hour. The precipitated solid was collected by filtration and washed with 75 mL of diisopropyl ether to obtain 92.7 g of a white solid. According to quantitative analysis conducted with high-performance liquid chromatography, 84.9 g (purity 91.6%) of the desired title compound was contained in the white solid (yield 74%, on the basis of 4-(1H-pyrazol-1-yl)benzylamine).

Physical properties of the resulting title compound were as follows.

CI-MS (m/z); 315 [M+1]

$^1$H-NMR (DMSO, δ (ppm)); 4.11 (2H, s), 6.53 (1H, dd, J=1.7 Hz), 7.33 (2H, d, J=8.8 Hz), 7.56-7.61 (4H, m), 7.70-7.74 (1H, m), 8.12-8.45 (2H, m), 8.47 (1H, s), 8.92-8.93 (1H, m).

IR (KBr cm$^{-1}$); 459, 487, 546, 561, 592, 615, 629, 650, 698, 719, 743, 766, 810, 900, 937, 1029, 1060, 1116, 1163 (S=O), 1194, 1209, 1250, 1321, 1333, 1393, 1419, 1466, 1526 (C=N), 1582, 1612, 2666, 2779, 2843, 3047, 3126, 3142, 3436 (N—H).

Elemental analysis; Calcd: C, 57.31%; H, 4.49%; N, 17.82%.

Found: C, 57.04%; H, 4.24%; N, 17.71%.

Example 2

Synthesis of N-benzylpyridine-3-sulfonamide

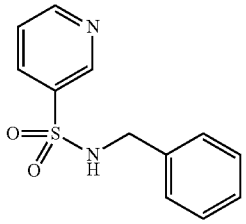 [SMILES: O=S(=O)(NCc1ccccc1)c1cccnc1]

In a glass vessel having an internal volume of approximately 25 mL and equipped with a stirrer and a thermometer, 23.9 mL of pyridine, 1.59 g of pyridine-3-sulfonic acid (9.99 mmol, Wako Pure Chemical Industries, Ltd.), and 0.159 g (1.30 mmol) of N,N-dimethyl-4-aminopyridine were mixed, 2.76 g of trifluoromethanesulfonic acid anhydride with a purity of 98% or more (9.8 mmol, Tokyo Chemical Industry Co., Ltd.) was added dropwise at 30° C. with stirring, and the mixture was stirred at the same temperature for 2 hours. Subsequently, to the reaction mixture was added 1.04 g of benzylamine (0.97 mmol, Tokyo Chemical Industry Co., Ltd.) at the same temperature over 30 minutes, and the mixture was stirred at the same temperature for 1 hour. The resulting reaction mixture was concentrated under reduced pressure, to the residue were added 40 mL of ethyl acetate and 33 mL of water to separate the layers. The organic layer was washed sequentially with 33 mL of a saturated aqueous ammonium chloride solution and 33 mL of water, and subsequently the organic layer was concentrated under reduced pressure. A procedure in which to the resulting residue was added 4.8 mL of diisopropyl ether and concentrated under reduced pressure was repeated twice, 17 ml of diisopropyl ether was further added, and the mixture was stirred at room temperature. The precipitated solid was collected by filtration, washed with 75 mL of diisopropyl ether, and vacuum-dried at room temperature to obtain 1.88 g of an orange-brown solid. According to quantitative analysis conducted with high-performance liquid chromatography, 1.52 g (purity 81.1%) of the desired title compound was contained in the resulting solid (quantitative yield 63%, on the basis of benzylamine).

Next, to 1.00 g of the resulting N-benzylpyridine-3-sulfonamide with purity 81.1% (net weight: 0.81 g, 3.3 mmol) were added 3.0 ml of a 4N aqueous sodium hydroxide solution, 3.0 ml of water and 3.2 g of toluene, and the mixture was stirred at room temperature for 1 hour. After insoluble matter was filtered, the layers were separated, and the resulting aqueous layer was washed with 1 ml of toluene. To the aqueous layer was added 5N hydrochloric acid until pH reached to a range of 3 to 4, and the mixture was stirred at room temperature for 30 minutes. The precipitated solid was filtered, washed with water, and subsequently vacuum-dried at 50° C. to obtain 0.78 g of a pale brown powder. According to analysis conducted with high-performance liquid chromatography, the desired compound N-benzylpyridine-3-sulfonamide was contained in the resulting powder at about 99.7% (yield 59%, on the basis of benzylamine).

Physical properties of the resulting N-benzylpyridine-3-sulfonamide were as follows.

CI-MS (m/z); 249 [M+1].

$^1$H-NMR (DMSO, δ (ppm)); 4.07 (2H, s), 7.20-7.29 (5H, m), 7.55-7.59 (1H, m), 8.10-8.13 (1H, m), 8.43 (1H, s), 8.77 (1H, dd, J=1.6 Hz, 4.8 Hz), 8.90 (1H, dd, J=0.7 Hz, 2.4 Hz).

IR (KBr cm$^{-1}$); 463, 529, 544, 587, 611, 629, 696, 747, 806, 817, 857, 903, 928, 992, 1028, 1036, 1072, 1111, 1123, 1168 (S=O), 1196, 1231, 1320, 1339, 1421, 1456, 1484, 1496, 1584, 1954, 2698, 2785, 2859, 3036, 3063, 3440 (N—H).

Elemental analysis; Calcd: C, 58.05%; H, 4.87%; N, 11.28%.

Found: C, 58.08%; H, 4.87%; N, 11.27%.

Example 3

Synthesis of N-[4-(1H-pyrazol-1-yl)benzyl]pyridine-2-sulfonamide

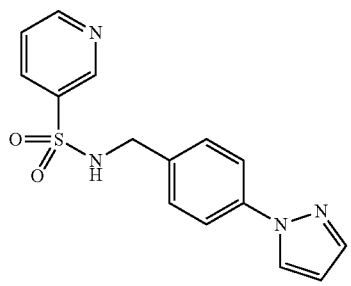 [SMILES: O=S(=O)(NCc1ccc(-n2cccn2)cc1)c1cccnc1]

In a glass vessel having an internal volume of approximately 50 mL and equipped with a stirrer and a thermometer, 23.9 mL of pyridine, 1.59 g of pyridine-2-sulfonic acid (10.0 mmol, Tokyo Chemical Industry), and 159 mg (1.30 mmol) of N,N-dimethyl-4-aminopyridine were mixed at room temperature, 2.76 g of trifluoromethanesulfonic acid anhydride (9.80 mmol, Tokyo Chemical Industry) was added dropwise at 30° C. with stirring, and the mixture was stirred at the same temperature for 2 hours. Then, 2.03 g (9.70 mmol) of 4-(1H-pyrazol-1-yl)benzylamine hydrochloride synthesized by a method similar to that described in Reference Example 2 was added dropwise to the reaction mixture at 30° C., and the mixture was stirred for 1 hour. The reaction mixture was left at room temperature overnight and subsequently concentrated under reduced pressure, and to the residue were added 39.8 mL of ethyl acetate and 33.4 mL of water to separate the layers. The resulting organic layer was washed with a 20% aqueous ammonium chloride solution and water and concentrated under reduced pressure. A procedure in which to the resulting residue was added 4.78 mL of diisopropyl ether and concentrated under reduced pressure was repeated twice. To the resulting residue was further added 16.7 mL of diisopropyl ether to triturate the solid material. The material was dispersed, subsequently filtered under reduced pressure, washed with diisopropyl ether, and vacuum-dried to obtain 2.66 g of a pale brown solid. According to quantitative analysis conducted with high-performance liquid chromatography, 2.46 g (92.5%) of the title compound was contained in a white solid (yield 80.7%, on the basis of 4-(1H-pyrazol-1-yl)benzylamine).

Physical properties of the resulting title compound were as follows (Data of the title compound synthesized in a similar manner were shown).

CI-MS (m/z); 315 [M+1].

$^1$H-NMR (DMSO, δ (ppm)); 4.20 (2H, s), 6.53 (1H, dd, J=2.4 Hz, 1.8 Hz), 7.35 (2H, d, J=8.7 Hz), 7.62-7.65 (1H, m), 7.72-7.74 (3H, m), 7.90-7.92 (1H, m), 8.02-8.04 (1H, m), 8.44-8.45 (2H, m), 8.71-8.73 (1H, m).

IR (KBr cm$^{-1}$); 417, 462, 495, 552, 593, 619, 648, 658, 720, 741, 760, 777, 809, 850, 892, 916, 936, 992, 1017, 1031, 1047, 1090, 1122, 1156, 1176 (S=O), 1203, 1232, 1253, 1296, 1316, 1331, 1361, 1398, 1410, 1429, 1443, 1452, 1526 (C=N), 1564, 1578, 1612, 1683, 1734, 1780, 1898, 2934, 3070, 3113, 3133, 3281, 3441 (N—H).

Elemental analysis; Calcd: C, 57.31%; H, 4.49%; N, 17.82%.

Found: C, 57.33%; H, 4.61%; N, 17.73%.

Example 4

Synthesis of N-butylpyridine-3-sulfonamide

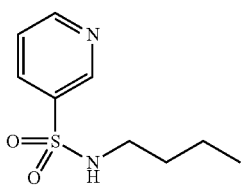

In a glass vessel having an internal volume of approximately 50 mL and equipped with a stirrer and a thermometer, 23.9 mL of pyridine, 1.59 g of pyridine-3-sulfonic acid (10.0 mmol, Wako Pure Chemical Industries), 159 mg (1.30 mmol) of N,N-dimethyl-4-aminopyridine were mixed at room temperature, 2.76 g of trifluoromethanesulfonic acid anhydride (9.80 mmol, Tokyo Chemical Industry) was added dropwise at 30° C. with stirring, and the mixture was stirred at the same temperature for 2 hours. Then, to the reaction mixture was added dropwise 709 mg of n-butylamine (9.70 mmol, Wako Pure Chemical Industries) at 30° C. over 30 minutes, and the mixture was stirred at the same temperature for 1 hour. After the reaction mixture was left at room temperature overnight and subsequently concentrated under reduced pressure, and to the residue were added 39.8 mL of ethyl acetate and 33.4 mL of water to separate the layers. The resulting organic layer was washed with a 20% aqueous ammonium chloride solution and water and concentrated under reduced pressure. A procedure in which to the resulting residue was added 4.78 mL of diisopropyl ether and concentrated under reduced pressure was repeated twice to obtain 1.63 g of a dark brown oil. According to quantitative analysis conducted with high-performance liquid chromatography, 1.34 g (82.4%) of the title compound was contained in the concentrated solution (yield 64.5%, on the basis of n-butylamine).

Physical properties of the resulting title compound were as follows (Data of the title compound synthesized in a similar manner were shown).

CI-MS (m/z); 215 [M+1].

$^1$H-NMR (DMSO, δ (ppm)); 0.79 (3, dd, J=7.3 Hz), 1.18-1.27 (2H, m), 1.31-1.38 (2H, m), 2.79 (2H, ddd, J=5.7 Hz), 7.63-7.67 (1H, m), 7.82 (1H, dd, J=5.2 Hz), 8.15-8.18 (1H, m), 8.82 (1H, dd, J=4.8 Hz, 1.6 Hz), 8.94 (1H, dd, J=2.4 Hz, 0.7 Hz).

IR (KBr cm$^{-1}$); 456, 572, 592, 622, 704, 742, 807, 866, 906, 981, 1026, 1085, 1109, 1122, 1166 (S=O), 1196, 1225, 1323, 1381, 1417, 1467, 1575 (C=N), 2874, 2935, 2961, 3095, 3287, 3580.

Elemental analysis; Calcd: C, 50.45%; H, 6.59%; N, 13.07%.

Found: C, 50.16%; H, 6.58%; N, 12.95%.

Example 5

Synthesis of N-[4-(1H-pyrazol-1-yl)benzyl]pyridine-3-sulfonamide

In a glass vessel having an internal volume of approximately 10 mL and equipped with a stirrer and a thermometer, 4.77 mL of pyridine, 318 mg of pyridine-3-sulfonic acid (2.00 mmol, Wako Pure Chemical Industries, Ltd.), and 31.8 mg (0.260 mmol) of N,N-dimethyl-4-aminopyridine were mixed, 330 mg of trifluoromethanesulfonic acid chloride with a purity of 98% or more (1.96 mmol, Tokyo Chemical Industry Co., Ltd.) was added dropwise at room temperature with stirring, and the mixture was stirred at 30° C. for 1 hour. Then, 407 mg (1.94 mmol) of 4-(1H-pyrazol-1-yl)benzylamine hydrochloride synthesized by a method similar to that described in Reference Example 2 was added portionwise to the reaction mixture at 30° C., and the mixture was stirred at the same temperature for 1 hour. After completion of the reaction, to the reaction mixture was added a mixed solution of acetonitrile/water (7/3 (V/V)) to make a homogeneous solution. According to quantitative analysis conducted with high-performance liquid chromatography, 246 mg of the desired compound was contained (reaction yield 40.4%).

Example 6

Synthesis of N-[4-(1H-pyrazol-1-yl)benzyl]pyridine-3-sulfonamide

In a glass vessel having an internal volume of approximately 10 mL and equipped with a stirrer and a thermometer, 4.77 mL of pyridine, 318 mg of pyridine-3-sulfonic acid (2.00 mmol, Wako Pure Chemical Industries, Ltd.), and 31.8 mg (0.260 mmol) of N,N-dimethyl-4-aminopyridine were mixed, 1.18 g of nonafluorobutanesulfonic acid anhydride with a purity of 97% (1.96 mmol, Sigma-Aldrich) was added dropwise at 30° C. with stirring, and the mixture was stirred at the same temperature for 1 hour. Then, 407 mg (1.94 mmol) of 4-(1H-pyrazol-1-yl)benzylamine hydrochloride synthesized by a method similar to that described in Reference Example 2 was added portionwise to the reaction mixture at 30° C., and the mixture was stirred at the same temperature for 2 hours. After completion of the reaction, to the reaction mixture was added a mixed solution of acetonitrile/water (7/3 (V/V)) to make a homogeneous solution. According to quantitative analysis conducted with high-performance liquid chromatography, 296 mg of the desired compound was contained (reaction yield 48.6%).

Example 7

Synthesis of N-[4-(1H-pyrazol-1-yl)benzyl]pyridine-3-sulfonamide

In a glass vessel having an internal volume of approximately 10 mL and equipped with a stirrer and a thermometer, 4.77 mL of pyridine and 318 mg of pyridine-3-sulfonic acid (2.00 mmol, Wako Pure Chemical Industries, Ltd.) were mixed, 553 mg of trifluoromethanesulfonic acid anhydride with a purity of 98% or more (1.96 mmol, Tokyo Chemical Industry Co., Ltd.) was added dropwise at room temperature with stirring, and the mixture was stirred at 30° C. for 1 hour. Then, 407 mg (1.94 mmol) of 4-(1H-pyrazol-1-yl)benzylamine hydrochloride synthesized by a method similar to that described in Reference Example 2 was added portionwise to the reaction mixture at 30° C., and the mixture was stirred at the same temperature for 1 hour. After completion of the reaction, according to quantitative analysis of the reaction mixture conducted with high-performance liquid chromatography, 570 mg of the desired compound was contained (reaction yield 93.5%).

Example 8

Synthesis of N-[4-(1H-pyrazol-1-yl)benzyl]pyridine-3-sulfonamide

In a glass vessel having an internal volume of approximately 10 mL and equipped with a stirrer and a thermometer, 4.77 mL of pyridine, 318 mg of pyridine-3-sulfonic acid (2.00 mmol, Wako Pure Chemical Industries, Ltd.), and 31.8 mg of N,N-dimethyl-4-aminopyridine (0.260 mmol) were mixed, 553 mg of trifluoromethanesulfonic acid anhydride with a purity of 98% or more (1.96 mmol, Tokyo Chemical Industry Co., Ltd.) was added dropwise at room temperature with stirring, and the mixture was stirred at 60° C. for 1 hour. Subsequently, 407 mg (1.94 mmol) of 4-(1H-pyrazol-1-yl)benzylamine hydrochloride synthesized by a method similar to that described in Reference Example 2 was added portionwise to the reaction mixture at 60° C., and the mixture was stirred at the same temperature for 1 hour. After completion of the reaction, the reaction solution was cooled to room temperature. According to quantitative analysis conducted with high-performance liquid chromatography, 577 mg of the desired compound was contained (reaction yield 94.5%).

Example 9

Synthesis of N-[4-(1H-pyrazol-1-yl)benzyl]pyridine-3-sulfonamide

In a glass vessel having an internal volume of approximately 10 mL and equipped with a stirrer and a thermometer, 4.77 mL of methylene chloride, 633 mg of pyridine (8.00 mmol, Wako Pure Chemical Industries, Ltd.), and 318 mg of pyridine-3-sulfonic acid (2.00 mmol, Wako Pure Chemical Industries, Ltd.) were mixed, 553 mg of trifluoromethanesulfonic acid anhydride with a purity of 98% or more (1.96 mmol, Tokyo Chemical Industry Co., Ltd.) was added dropwise at room temperature with stirring, and the mixture was stirred at 30° C. for 1 hour. Then, 407 mg (1.94 mmol) of 4-(1H-pyrazol-1-yl)benzylamine hydrochloride synthesized by a method similar to that described in Reference Example 2 was added portionwise to the reaction mixture at 30° C., and the mixture was stirred at the same temperature for 1 hour. After completion of the reaction, to the reaction mixture was added a mixed solution of acetonitrile/water (7/3 (V/V)) to make a homogeneous solution. According to quantitative analysis conducted with high-performance liquid chromatography, 494 mg of the desired compound was contained (reaction yield 81.0%).

Example 10

Synthesis of N-[4-(1H-pyrazol-1-yl)benzyl]pyridine-3-sulfonamide

In a glass vessel having an internal volume of approximately 10 mL and equipped with a stirrer and a thermometer, 4.77 mL of acetonitrile, 316 mg of pyridine (4.00 mmol, Wako Pure Chemical Industries, Ltd.), and 318 mg of pyridine-3-sulfonic acid (2.00 mmol, Wako Pure Chemical Industries, Ltd.) were mixed, 553 mg of trifluoromethanesulfonic acid anhydride with a purity of 98% or more (1.96 mmol, Tokyo Chemical Industry Co., Ltd.) was added dropwise at 10° C. with stirring, and the mixture was stirred at the same temperature for 1 hour. Then, 407 mg (1.94 mmol) of 4-(1H-pyrazol-1-yl)benzylamine hydrochloride synthesized by a method similar to that described in Reference Example 2 was added portionwise to the reaction mixture at 10° C., and the mixture was stirred at the same temperature for 2 hours. Then, to the reaction mixture was added dropwise 158 mg of pyridine (2.00 mmol, Wako Pure Chemical Industries, Ltd.) at 10° C., the mixture was stirred at the same temperature for 1 hour, 158 mg of pyridine (2.00 mmol, Wako Pure Chemical Industries, Ltd.) was further added dropwise at 10° C., and the mixture was stirred at the same temperature for 1 hour. The reaction mixture was warmed to 20° C. and stirred at the same temperature for 1 hour, and subsequently to the reaction mixture was added a mixed solution of acetonitrile/water (7/3 (V/V)) to make a homogeneous solution. According to quantitative analysis conducted with high-performance liquid chromatography, 470 mg of the desired compound was contained (reaction yield 77.1%).

Example 11

Synthesis of N-[4-(1H-pyrazol-1-yl)benzyl]pyridine-3-sulfonamide

In a glass vessel having an internal volume of approximately 10 mL and equipped with a stirrer and a thermometer, 4.77 mL of acetonitrile, 633 mg of pyridine (8.00 mmol, Wako Pure Chemical Industries, Ltd.), and 318 mg of pyridine-3-sulfonic acid (2.00 mmol, Wako Pure Chemical Industries, Ltd.) were mixed, 553 mg of trifluoromethanesulfonic acid anhydride with a purity of 98% or more (1.96 mmol, Tokyo Chemical Industry Co., Ltd.) was added dropwise at room temperature with stirring, and the mixture was stirred at 60° C. for 1 hour. Subsequently, 407 mg (1.94 mmol) of 4-(1H-pyrazol-1-yl)benzylamine hydrochloride synthesized by a method similar to that described in Reference Example 2 was added portionwise to the reaction mixture at 60° C., and the mixture was stirred at the same temperature for 1 hour. After completion of the reaction, the reaction solution was cooled to room temperature. According to quantitative analysis conducted with high-performance liquid chromatography, 598 mg of the desired compound was contained (reaction yield 98.1%).

Reference Example 1

Synthesis of 4-(1H-pyrazol-1-yl)benzonitrile

In a glass vessel having an internal volume of approximately 1 L and equipped with a stirrer, a thermometer and a top cooling tube, 121 g (1.00 mol) of 4-fluorobenzonitrile, 81.9 g (1.20 mol) of pyrazole, 165 g (1.19 mol) of potassium carbonate, and 320 mL of dimethylsulfoxide were mixed at room temperature, and the mixture was allowed to react between 115° C. and 120° C. for 7 hours and subsequently left at room temperature overnight. After 500 mL of water and 500 mL of toluene were added and the mixture was stirred, the mixture was filtered, the filtrate was separated into layers, the aqueous layer was subsequently re-extracted with 300 mL of toluene, and the resulting mixed organic layers were combined and concentrated under reduced pressure until the internal volume was 223 g. After 300 mL of diisopropyl ether was added and the mixture was stirred for 30 minutes in an ice bath, the mixture was filtered, and the residue was dried at 50° C. to obtain 148 g of the title compound as a pale yellow solid. (yield 87.7%, on the basis of 4-fluorobenzonitrile).

Physical properties of the resulting title compound were as follows (Data of the title compound synthesized in a similar manner were shown).

CI-MS (m/z); 170 [M+1].

$^1$H-NMR (CDCl$_3$, δ (ppm)); 6.53-6.55 (1H, m), 7.74-7.78 (3H, m), 7.84 (1H, dd, J=2.1 Hz), 7.86 (1H, dd, J=2.1 Hz), 8.00 (1H, d, J=2.6 Hz).

IR (KBr cm$^{-1}$); 446, 546, 573, 607, 652, 714, 750, 771, 814, 836, 884, 913, 936, 962, 1032, 1044, 1053, 1128, 1177, 1186, 1200, 1253, 1316, 1344, 1393, 1407, 1438, 1514, 1529, 1611, 1657, 2228 (CN), 3067, 3138, 3154, 3421.

Elemental analysis; Calcd: C, 70.99%; H, 4.17%; N, 24.84%.

Found: C, 71.17%; H, 4.28%; N, 24.88%.

Reference Example 2

Synthesis of 4-(1H-pyrazol-1-yl)benzylamine hydrochloride

To a glass vessel having an internal volume of approximately 2 L and equipped with a stirrer and a thermometer were added 70.0 g (0.414 mol) of 4-(1H-pyrazol-1-yl)benzonitrile and 826 mL of ethanol, and the inside of the vessel was subjected to argon replacement. Then, 40.2 mL (0.482 mol) of concentrated hydrochloric acid and 7 g of 5% palladium carbon (approximately 50% hydrous product, N.E. CHEMCAT Corporation, STD type) were added, and the inside of the reaction vessel was subjected to hydrogen replacement. The reaction mixture was allowed to react under a slightly compressed hydrogen atmosphere at 26° C. to 38° C. for about 7.5 hours, the inside of the vessel was subjected to nitrogen replacement, and the vessel was subsequently left for about 2.5 days at room temperature. After 500 mL of water was added, the mixture was filtered through Celite, the filtrate was concentrated until the fluid volume was 497 g, 165 mL of ethanol was subsequently added, and the solution was concentrated until the fluid volume was 371 g. Again, 165 mL of ethanol was added, the solution was concentrated until the fluid volume was 198 g, 180 mL of acetonitrile was subsequently added, the solution was left at approximately 5° C. overnight and subsequently filtered, and insoluble matter was washed with 90 mL of acetonitrile. The resulting residue was air-dried for about 1 hour and subsequently dried at 50° C. under reduced pressure to obtain 61.0 g of the title compound as a white solid. (yield 70.3%, on the basis of 4-(1H-pyrazol-1-yl)benzonitrile).

Physical properties of the resulting title compound were as follows (Data of the title compound synthesized in a similar manner were shown).

CI-MS (m/z); 174 [M+1].

$^1$H-NMR (DMSO, δ (ppm)); 4.05 (2H, s), 6.56 (1H, dd, J=2.4 Hz, 1.8 Hz), 7.63 (2H, d, J=8.6 Hz), 7.76 (1H, d, J=1.6 Hz), 7.88-7.91 (2H, m), 8.53-8.55 (4H, m).

IR (KCl cm$^{-1}$); 448, 461, 538, 613, 635, 654, 725, 750, 766, 795, 835, 882, 915, 939, 971, 1034, 1055, 1079, 1120, 1208, 1219, 1254, 1318, 1338, 1382, 1397, 1414, 1444, 1470, 1485, 1532, 1597, 1615, 1673, 1728, 1919, 2047, 2224, 2359, 2554, 2584, 2696, 2758, 2897, 2971, 3000, 3113, 3134, 3412.

Elemental analysis; Calcd: C, 57.28%; H, 5.77%; N, 20.04%.

Found: C, 57.30%; H, 5.77%; N, 20.08%.

INDUSTRIAL APPLICABILITY

The present invention relates to a mixed sulfonic acid anhydride obtained from a heteroaromatic sulfonic acid compound and a perfluoroalkyl sulfonic acid anhydride or a perfluoroalkyl sulfonic acid halide, and a method for producing a heteroaromatic sulfonamide compound by reacting the mixed sulfonic acid anhydride obtained with amine. The method for producing the heteroaromatic sulfonamide compound of the present invention is safer than conventional methods, and also provides a higher yield and fewer byproducts, so that the method is very useful in industry. Further, the heteroaromatic sulfonamide compound obtained by the present production is a useful compound as an intermediate and an active ingredient for a drug.

The invention claimed is:

1. A method for producing a sulfonamide compound of the general formula (4):

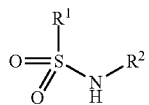

(4)

wherein
R¹ is a pyridyl group which is unsubstituted or substituted; and
R² is an alkyl group, an alkenyl group, an alkynyl group, a cycloalkyl group, an aryl group, a heteroaryl group, an aralkyl group or a heteroarylalkyl group, which is unsubstituted or substituted,
comprising the steps of:
(A) reacting a sulfonic acid compound of the general formula (2):

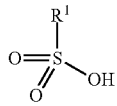 (2)

wherein
R¹ is as defined above,
with a sulfonylating agent selected from the group consisting of a perfluoroalkyl sulfonic acid anhydride or a perfluoroalkyl sulfonic acid halide to yield a mixed sulfonic acid anhydride of the general formula (1):

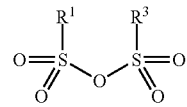 (1)

wherein
R¹ is as defined above and R³ is a perfluoroalkyl group; and
(B) subsequently conducting a reaction by adding an amine compound of the general formula (3);

 (3)

wherein
R² is as defined above,
to the reaction solution obtained in the step (A).

* * * * *